United States Patent [19]

Müller

[11] 3,932,510

[45] Jan. 13, 1976

[54] PROCESS FOR THE PREPARATION OF CYCLOHEXANEDIONES-(1,3)

[75] Inventor: Werner H. Müller, Kelkheim, Germany

[73] Assignee: Hoechst Aktiengesellschaft, Frankfurt am Main, Germany

[22] Filed: Dec. 13, 1973

[21] Appl. No.: 424,308

[30] Foreign Application Priority Data

Dec. 16, 1972 Germany............................ 2261751

[52] U.S. Cl............ 260/586 R; 260/343.5; 260/590
[51] Int. Cl.²......................................... C07C 45/00
[58] Field of Search........................ 260/586 R, 590

[56] References Cited
UNITED STATES PATENTS

| | | | |
|---|---|---|---|
| 2,510,364 | 6/1950 | Bankert...................... | 260/586 R X |
| 3,652,596 | 3/1972 | Fried........................... | 260/586 R X |
| 3,676,430 | 7/1972 | Capp et al................... | 260/586 R X |

OTHER PUBLICATIONS

Shusherina et al., "Chem. Ab.," Vol. 66, p. 94714x, (1967).
"DuPont DMF (Dimethylforamide) Product Information", p. 14., (1970), No. A 65510.
"Dimethylsulfoxide as a Reaction Solvent," Crown Zellerback, Chem. Prod. Div. p. 23, (1968).

*Primary Examiner*—Norman Morgenstern
*Attorney, Agent, or Firm*—Curtis, Morris & Safford

[57] ABSTRACT

A process for the preparation of cyclohexanediones-(1,3) by isomerization of a δ-enol-lactone in the presence of a strong base and a carboxylic acid amide, phosphoric acid amide, sulfoxide or sulfone as solvent.

4 Claims, No Drawings

PROCESS FOR THE PREPARATION OF CYCLOHEXANEDIONES-(1,3)

The present invention relates to the preparation of cyclohexanediones-(1,3).

It is known to prepare cyclohexanediones-(1,3 by the isomerization of δ-enol-lactones having a double bond in the ring or in a semi-cyclic position with sodium alcoholates in benzene.

An essential disadvantage of these methods are their poor selectivity, low space-time yields and difficult isolation of the cyclic diketones from the reaction products, which are obtained in an oily form, and which also contain by-products preventing crystallization. These drawbacks therefore prevent an economic manufacture of the cyclohexanediones-(1,3).

The cyclohexanediones-(1,3) can be converted to industrially important resorcinols by dehydrogenation.

The present invention now provides a process for the preparation of cyclohexandiones-(1,3) of the formula

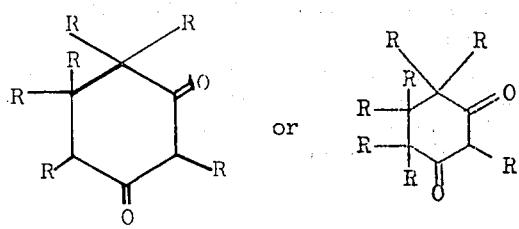

where the single radicals R are the same or different and each represent a hydrogen atom or an alkyl or aryl group, by isomerization of, respectively, a δ-enol-lactone having a cyclic or semicyclic double bond and corresponding to the formulae

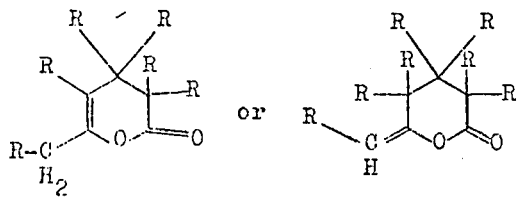

where R is as defined above, in the presence of a solvent, with a strong base, wherein the solvent contains at least 50 % of a compound belonging to one of the following classes of substances:

1. carboxylic acid amides of the formula

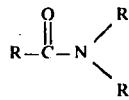

where the single radicals R are the same or different and each represent a hydrogen atom or an alkyl or aryl group;

2. phosphoric acid amides of the formula

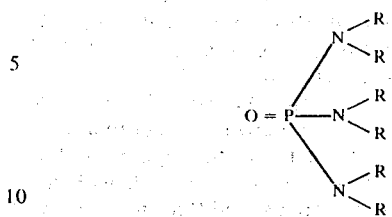

where R is as defined above;

3. sulfoxides or sulfones of the formula

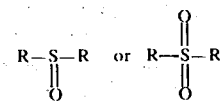

where R is alkyl or aryl.

As the strong base acting as an isomerization agent, alkali metal or alkaline earth metal alcoholates, amides or hydrides may be used. Also alkali or alkaline earth metals per se or their amalgams are suitable, as well as alcoholic solutions of the alcoholates.

Especially suitable carboxylic acid amide solvents, which also have an accelerating effect on the isomerization reaction, are dimethyl formamide (DMF), dimethyl acetamide (DMAC) or N-methylpyrrolidone (NMP).

Among the phosphoric acid amides, an especially appropriate solvent is hexamethyl-phosphoric acid triamide.

From the class of sulfoxides and sulfones, dimethyl sulfoxide (DMSO) and sulfolane are preferably used as solvents.

The carboxylic acid amides, phosphoric acid amides, sulfoxides, and sulfones may be used in admixture with other solvents. The amount of the latter is generally up to 30 %, but it may be increased up to 50 %. Suitable mixture components are for example methanol, diethyl ether, acetonitrile, and benzene.

The isomerization reaction is generally carried out at a temperature of from 0° to 150°C, preferably from 15° to 70°C, without pressure and continuously or discontinuously. The solvent is generally used in a 10 to 10,000 fold excess, relative to the starting lactone. After recycling, the solvents may be used again.

The reaction proceeds with high selectivity (more than 95 %) and high space-time yield (more than 300 g/l. hr). Crystallized products having a high degree of purity are obtained. The reaction can be described by the following scheme, when for example 6-methyl-3,4-dihydro-2-pyranone is used:

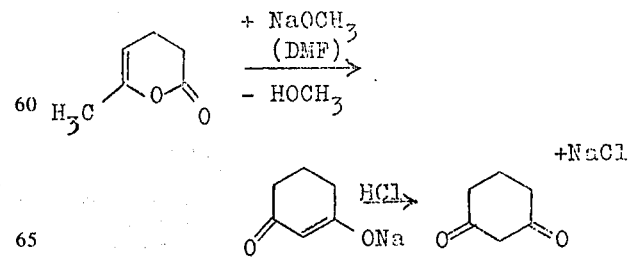

The following δ-enol-lactones are especially suitable as starting compounds: 6-methyl-3,4-dihydro-2-pyranone; 5,6-dimethyl-3,4-dihydro-2-pyranone; 6-methyl-5-phenyl-3,4-dihydro-2-pyranone; and 5,5-dimethyl-6-methylene-tetrahydro-2-pyranone.

The reaction may for example be carried out as follows: the lactone to be isomerized is continuously added to a mixture of the isomerization agent and the solvent already present in a reaction vessel, with intense agitation and with such a speed that the concentration of free lactone remains at a low level. Since the solvents in accordance with the present invention considerably accelerate the reaction rate, feeding-in can be carried out very rapidly and thus space-time yields of from 300 to 600 g/l. hr may be attained without difficulty. As soon as an amount of lactone equimolar to the condensation agent is added, the solvent is eliminated in vacuo. The salt obtained as residue is dissolved in a certain amount of water, and the solution is acidified with concentrated acid. On cooling, the cyclic diketones precipitate in a pure crystallized form. A small percentage may be obtained in addition by extraction from the aqueous mother liquor. The net yields after recrystallization are superior to 95 %.

The following Examples illustrate the invention

EXAMPLES 1 TO 10

A mixture of isomerization agent and solvent is introduced into a 1 liter four-necked flask provided with mechanical agitator, dropping funnel, thermometer and reflux condenser. An amount of the unsaturated lactone equimolar to the isomerization agent, dissolved in a certain amount of solvent, is added dropwise and homogeneously. The temperature is controlled by cooling, if necessary. The conversion is observed by means of gas chromatography. As long as free isomerization agent is present, the conversion is practically momentary.

After complete reaction, the solvent is eliminated in vacuo, the residue is digested with ether, dissolved in a small amount of water, and the solution is acidified with concentrated hydrochloric acid.

When benzene is used as solvent (Example 1), a yellow-brown oil is separated by acidification of the aqueous alkali metal salt solution, from which oil a small amount of dihydroresorcinol is obtained by complicated crystallization. The yield is 37 %. However, when the reaction is carried out in DMF, DMSO or DMAC (Examples 2, 3, and 5), a practically pure, crystallized dihydroresorcinol is obtained with high yields on acidification with cooling by ice. The same goes for the use of DMF/methanol and DMF/diethyl ether mixtures.

A small amount may be additionally obtained from the aqueous phase by extraction with methylene chloride. After recrystallization from benzene or ethyl acetate, the yield is superior to 95 %.

| Examples 1 to 7 | | | Isomerization of 6-methyl-3,4-dihydro-2-pyranone (MDP) to dihydroresorcinol | | | |
|---|---|---|---|---|---|---|
| Example | Solvent | (1) ml | MDP(2) Solvent g/ml | Isomerization agent Kind | g | Reaction time min. |
| 1 | Benzene | 450 | 37.5/50 | NaOCH$_3$ | 30 | 480 |
| 2 | DMF | 250 | 37.5/50 | NaOCH$_3$ | 20 | 30 |
| 3 | DMSO | 250 | 37.5/100 | NaOCH$_3$ | 20 | 60 |
| 4 | DMSO | 250 | 37.5/100 | NaH | 10 | 60 |
| 5 | DMAC | 250 | 37.5/100 | NaOCH$_3$ | 20 | 60 |
| 6 | DMF/methanol 5 : 1 | 240 | 37.5/80 | NaOCH$_3$ | 20 | 60 |
| 7 | DMF/diethyl ether 5 : 1 | 240 | 37.5/80 | NaOCH$_3$ | 20 | 60 |

| Example | Temperature °C | H$_2$O (3) ml | conc. HCL (4) ml | Yield (5) % of the theor. yield | STY g/l.h(6) | Mp °C |
|---|---|---|---|---|---|---|
| 1 | 25–80.1 | 50 | 46 | 37 | 3 | 103 |
| 2 | 25 | 55 | 31 | 96.3 | 217 | 104 |
| 3 | 23 | 50 | 31 | 93.6 | 87 | 104 |
| 4 | 25 | 50 | 31 | 94.5 | 88 | 104 |
| 5 | 25 | 55 | 31 | 90.0 | 84 | 105 |
| 6 | 25 | 50 | 31 | 33.0 | 83 | 103 |
| 7 | 25 | 50 | 31 | 92.0 | 93 | 104 |

6;7

(1) introduced first (2) g MDP per ml of solvent in dropping funnel;

(3) H$_2$O added for dissolving the Na-dihydroresorcinol;

(4) conc. hydrochloric acid for precipitating the cyclic dione;

(5) yield after recrystallization from benzene;

(6) space-time yield

Examples 8, 9 — Isomerization of δ-enol lactones having a double bond in the ring

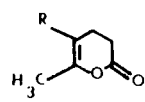

| Example | R | Solvent (1) DMF ml | Lactone/DMF g/ml | Isomerization agent NaOCH₃ g | Reaction time min |
|---|---|---|---|---|---|
| 8 | CH₃ | 250 | 42/100 | 20 | 60 |
| 9 | φ | 250 | 63/100 | 20 | 60 |

Isomerization of δ-enol lactones having a semicyclic double bond

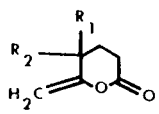

| Example | R₁ | R₂ | Solvent (1) | Lactone/DMF g/ml | Isomerization agent NaOCH₃ g | Reaction time min |
|---|---|---|---|---|---|---|
| 10 | CH₃ | CH₃ | 250 | 46.7/100 | 20 | 60 |

| Example | Temperature °C | H₂O (3) ml | conc. HCl (4) ml | Yield (5) % of the theor. yield | STY (6) g/l.h | MP °C | BP 8 torrs °C |
|---|---|---|---|---|---|---|---|
| 8 | 35 | 60 | 31 | 93.5 | 99 | | 135–136 |
| 9 | 35 | 60 | 31 | 95.0 | 144 | 112 | |
| 10 | 35 | 60 | 31 | 96.0 | 110 | 103 | |

What is claimed is:

1. In a method for the preparation of 1,3-cyclohexanediones of the formulas

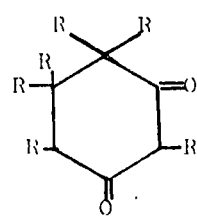 or 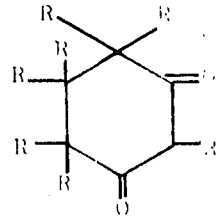

wherein the R's are the same or different and each represents hydrogen, alkyl, or aryl, by the isomerization, with a strong base, in the presence of a solvent, of, respectively, a δ-enol lactone having a cyclic or semicyclic double bond and having the formula

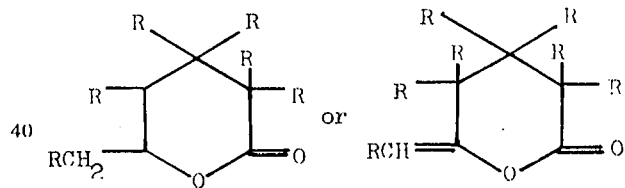

the improvement wherein said solvent comprises at least 50 percent of a member selected from the group consisting of dimethyl formamide, dimethyl acetamide, N-methyl-pyrrolidone, hexamethyl-phosphoric acid triamide, dimethyl sulfoxide, and sulfolane, the balance of said solvent being methanol, diethyl ether, acetonitrile, or benzene.

2. A method as in claim 1 wherein said solvent comprises 100 percent of a member selected from the group consisting of dimethyl formamide, dimethyl acetamide, N-methyl pyrrolidone, hexamethyl-phosphoric acid triamide, dimethyl sulfoxide, and sulfolane.

3. A method as in claim 1 wherein the isomerization is carried out at a temperature between 0°C. and 150°C.

4. A method as in claim 1 wherein said strong base is an alkali or alkaline earth metal or an amalgam, alcoholate, amide or hydride thereof.

* * * * *